United States Patent
Kronfeld et al.

(10) Patent No.: US 8,585,858 B2
(45) Date of Patent: Nov. 19, 2013

(54) MEDICAL CATHETER WITH BUMP TUBING PROXIMAL SEGMENT

(76) Inventors: Alex M. Kronfeld, North East, MD (US); Derek L. Norton, Joppa, MD (US); Robin M. Young, Abingdon, MD (US)

( * ) Notice: Subject to any disclaimer, the term of this patent is extended or adjusted under 35 U.S.C. 154(b) by 16 days.

(21) Appl. No.: 13/153,564

(22) Filed: Jun. 6, 2011

(65) Prior Publication Data
US 2012/0310213 A1    Dec. 6, 2012

(51) Int. Cl.
B29C 65/02    (2006.01)

(52) U.S. Cl.
USPC ..... 156/304.6; 156/203; 604/529; 604/103.1; 604/533

(58) Field of Classification Search
USPC .............. 604/523, 526, 529, 96.01, 533, 103, 604/103.1; 156/173, 296, 203, 304.6, 157
See application file for complete search history.

(56) References Cited

U.S. PATENT DOCUMENTS

| | | | |
|---|---|---|---|
| 5,658,263 A | 8/1997 | Dang et al. | |
| 5,951,539 A * | 9/1999 | Nita et al. | 604/526 |
| 6,106,510 A | 8/2000 | Lunn et al. | |
| 7,896,861 B2 | 3/2011 | McFerran et al. | |
| 2004/0140585 A1* | 7/2004 | Sterud et al. | 264/230 |
| 2005/0004523 A1 | 1/2005 | Osborne et al. | |
| 2006/0030835 A1* | 2/2006 | Sherman et al. | 604/526 |
| 2006/0074477 A1 | 4/2006 | Berthiaume et al. | |
| 2006/0239982 A1 | 10/2006 | Simpson | |
| 2007/0016132 A1 | 1/2007 | Oepen et al. | |
| 2008/0103483 A1 | 5/2008 | Johnson et al. | |
| 2009/0312786 A1 | 12/2009 | Trask et al. | |
| 2010/0324567 A1 | 12/2010 | Root et al. | |

FOREIGN PATENT DOCUMENTS

| | | |
|---|---|---|
| EP | 1165167 B1 | 11/2008 |
| WO | WO9215356 | 9/1992 |

OTHER PUBLICATIONS

Shana Leonard, Extrusion Process Bumps Catheter Design to the Next Level, Mar. 7, 2011, pp. 1-4.

\* cited by examiner

*Primary Examiner* — Katarzyna Wyrozebski Lee
*Assistant Examiner* — Vishal I Patel

(57) ABSTRACT

A medical catheter for inserting into a body includes a bump tubing section with proximal and distal ends, wherein the proximal end is configured to mate with a hub. The bump tubing section has an intermediate portion extending away from the proximal end with a substantially constant outer diameter and thickness, and a taper portion adjacent the distal end with generally decreasing inside and outside diameters to provide a gradually increasing flexibility toward the distal end of the bump tubing section. The bump tubing section is comprised of a polymer having a predetermined flexural modulus. A tip section is disposed distally of the distal end of the bump tubing section comprising a distal liner and a distal cover such that at least a majority of the tip section has a substantially constant stiffness and a flexural modulus substantially equal to or greater than the predetermined flexural modulus.

4 Claims, 5 Drawing Sheets

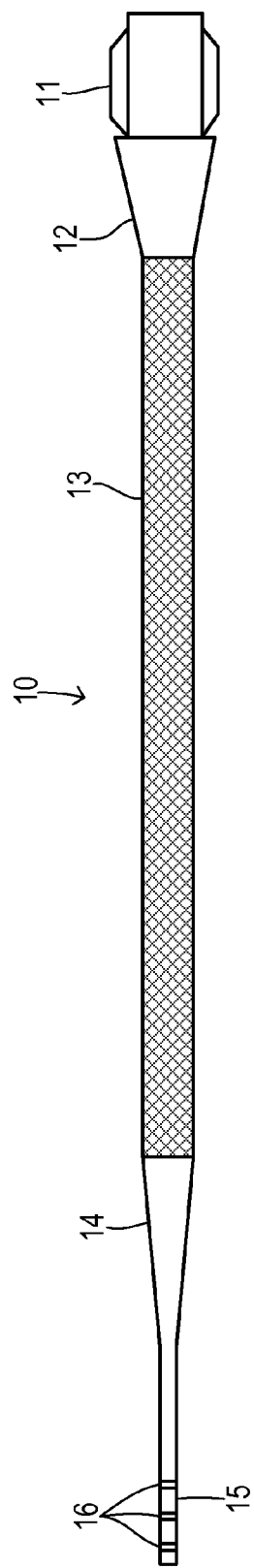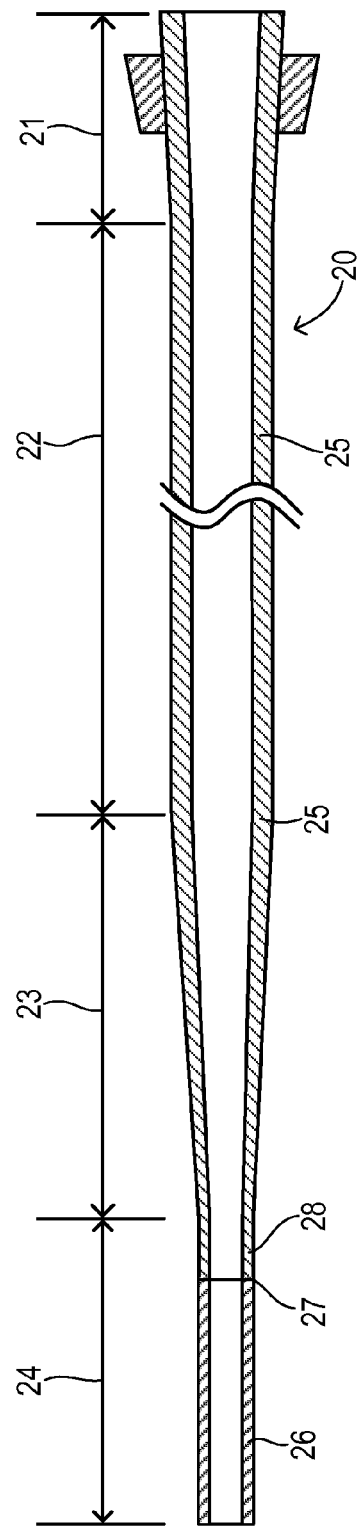

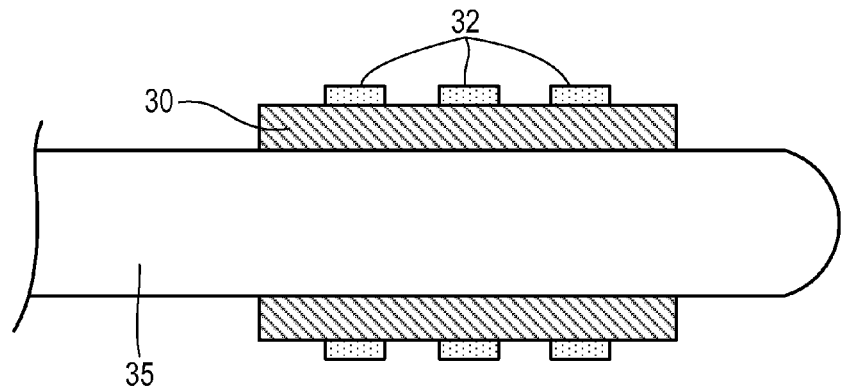
Fig. 4
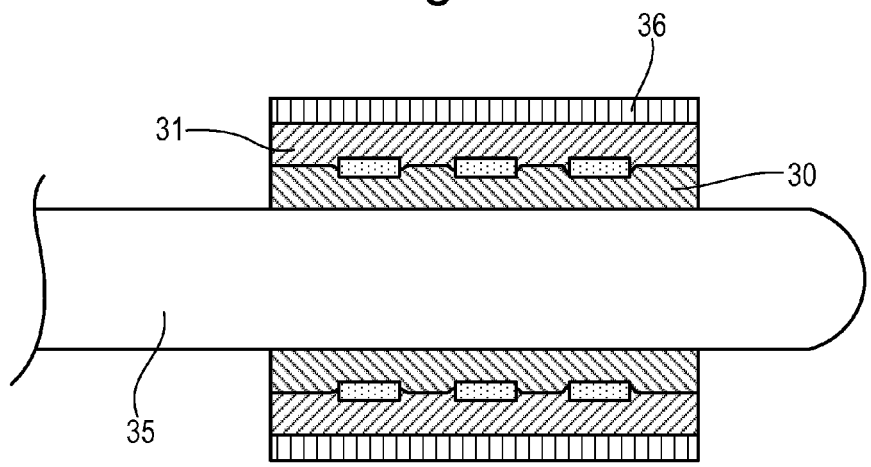
Fig. 5
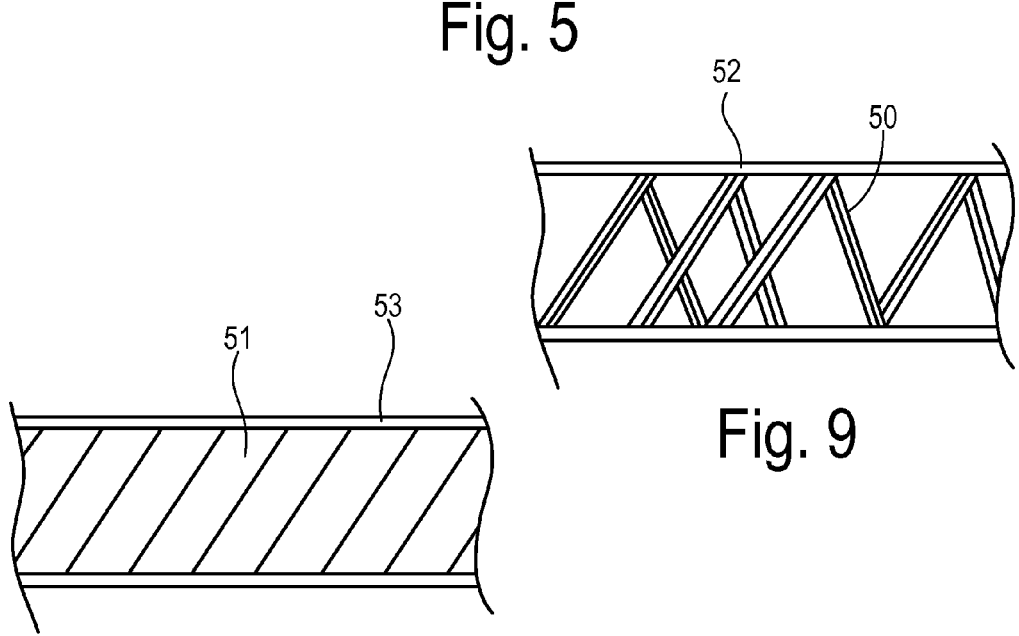
Fig. 9
Fig. 10

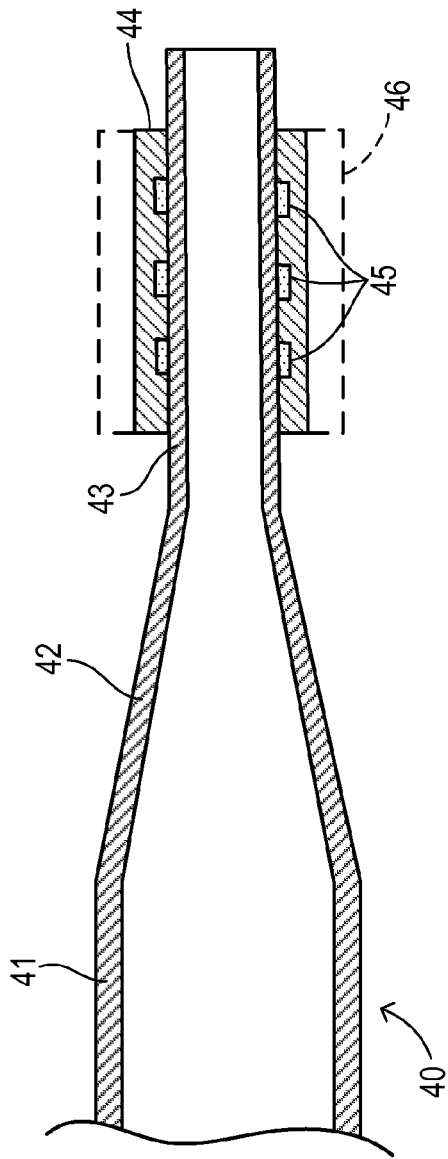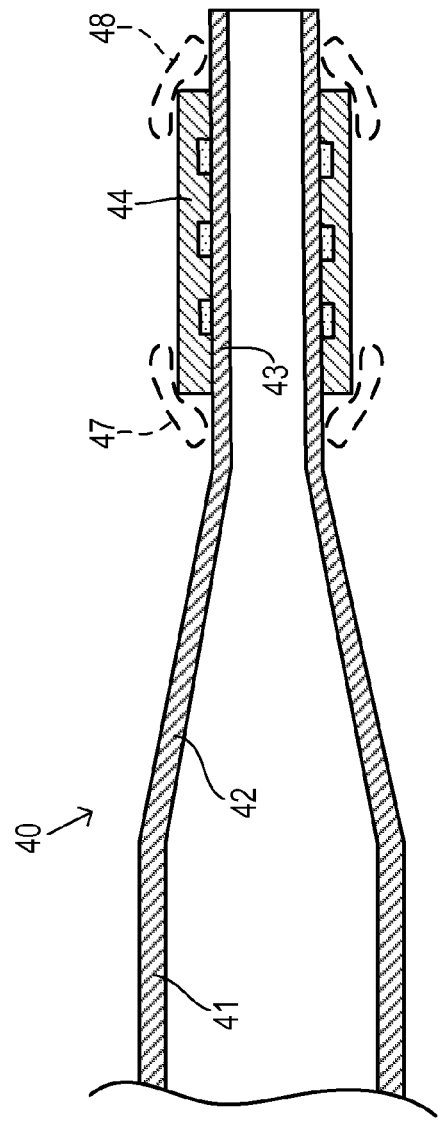

MEDICAL CATHETER WITH BUMP TUBING PROXIMAL SEGMENT

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to a medical catheter with multiple stiffness sections, and, more specifically, to a medical catheter and an efficient manufacturing method employing bump tubing and a relatively stiffened distal end incorporating radiopaque markers.

Many medical procedures require entry into a patient's blood vessel for purposes of accessing a desired site, e.g., angioplasty, stenting, and other treatments for chronic total occlusions. In order to gain access to the desired site, a catheter is advanced through the blood vessel. Once in place within the patient's vessel, various types of medical instrumentation can be fed through the catheter and positioned at the desired site so that the procedure may be performed.

To initially gain access to a particular site within a patient, a needle is used to puncture the patient's skin and gain entry to a desired blood vessel. During insertion of the catheter through the blood vessels, it may be required to follow a tortuous path. Therefore, the distal end of the catheter has been made more flexible than the proximal end. The flexible distal end provides trackability, while the stiffer proximal end provides pushability. As shown in U.S. Pat. No. 7,896,861, a catheter may include a proximal shaft section of a polymer with a relatively high durometer and a distal shaft section of a polymer with a relatively low durometer. However, mechanical bonding or welding of the different sections creates a potential site for kinking of the catheter.

Bump tubing has been used in catheters to provide a decreased tube diameter at the distal end for navigating small vessels and to provide an increased tube diameter at the proximal end for accommodating medical devices to be used during a medical procedure. Bump tubing, also known as a taper tube, may be formed by extruding a polymeric tube in a manner that varies the diameter during the extrusion. As a consequence of the changing diameter, the tube stiffness is reduced along with the diameter without creating a potential site for kinking.

To assist in locating the distal tip by fluoroscopy during a procedure, radiopaque markers are applied to the distal tip. Platinum or platinum blends have been applied to the tubing for this purpose. However, previous markers have been subject to wear and other damage while passing through particularly tortuous anatomies.

It would be desirable to combine the use of bump tubing with efficient assembly methods that lower the risk of kinking and provide protection for radiopaque markers.

SUMMARY OF THE INVENTION

The present invention includes the discovery that performance may be improved if the distal tip is not made to be the softest, most flexible portion of the catheter because the softer grades of plastics being used have an increased coefficient of friction. Instead, a transition zone with increasing flexibility is located proximal to a distal tip, the distal tip having substantially constant stiffness and a flexural modulus substantially the same as or greater than the transition zone. The transition zone is comprised of a bump tubing section wherein both the inside and outside diameters are decreasing. A distal cover protects any radiopaque markers. Further, a fusing process employing shrink tubing may be used to join separate components with reduced kinking.

In one aspect of the invention, a catheter is provided for inserting into a body. A bump tubing section has proximal and distal ends, wherein the proximal end is configured to mate with a hub. The bump tubing section has an intermediate portion extending away from the proximal end with a substantially constant outer diameter and thickness, and a taper portion adjacent the distal end with generally decreasing inside and outside diameters to provide a gradually increasing flexibility toward the distal end of the bump tubing section. The bump tubing section is comprised of a polymer having a predetermined flexural modulus. A tip section is disposed distally of the distal end of the bump tubing section comprising a distal liner and a distal cover such that at least a majority of the tip section has a substantially constant stiffness and a flexural modulus substantially equal to or greater than the predetermined flexural modulus.

In another aspect of the invention, a catheter is provided for inserting into a body. A bump tubing section has proximal and distal ends, wherein the proximal end is configured to mate with a hub. The bump tubing section has an intermediate portion extending away from the proximal end with a substantially constant outer diameter and thickness, and a taper portion adjacent the distal end with generally decreasing inside and outside diameters to provide a gradually increasing flexibility toward the distal end of the bump tubing section. The bump tubing section is comprised of a polymer having a predetermined flexural modulus A tip section is disposed distally of the distal end of the bump tubing section comprising a distal liner and a distal cover such that at least a majority of the tip section has a substantially constant inside diameter and outside diameter. Radiopaque markers are disposed between the distal liner and the distal cover.

BRIEF DESCRIPTION OF THE DRAWINGS

FIG. 1 is a plan view of a catheter according to one embodiment of the present invention.

FIG. 2 is a cross-sectional view of a catheter of the invention.

FIG. 4 is a partial cross section showing the application of radiopaque markers during the manufacturing of a catheter.

FIG. 5 is a partial cross section showing the fusing of a distal cover and distal liner around the radiopaque markers.

FIGS. 7 and 8 illustrate the fusing of a distal cover in an embodiment wherein the distal liner is comprised of an extension of the bump tubing section.

FIG. 9 shows a partial braiding pattern for covering a portion of the is catheter.

FIG. 10 shows a coil pattern for covering a portion of the catheter.

DETAILED DESCRIPTION OF PREFERRED EMBODIMENTS

Figure 3:
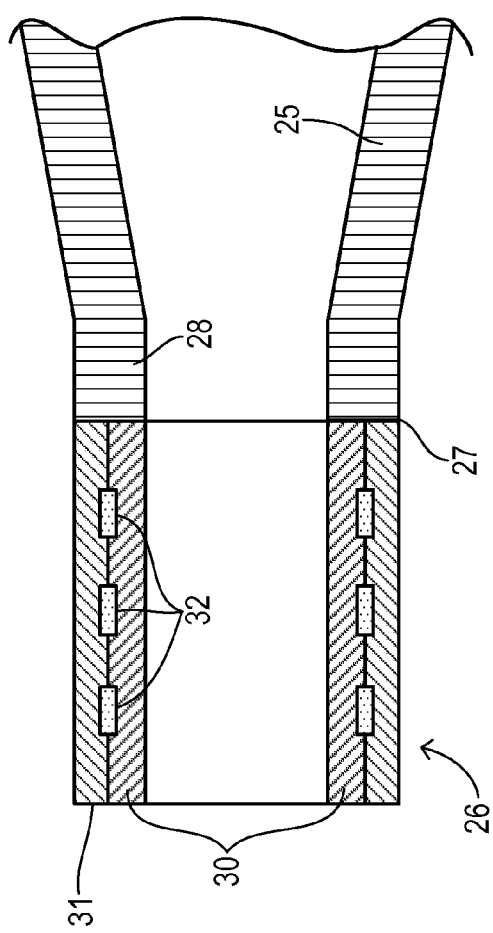
FIG. 3 is a cross-sectional view showing a distal end of a catheter of the invention in greater detail.

Referring now to FIG. 1, a catheter 10 has a proximal end having a hub 11 and a stress release section 12 of conventional design. A bump tubing section spanning the major portion of catheter 10 includes an intermediate portion 13 with a substantially constant outer diameter and thickness and a taper portion 14 with a generally decreasing inside and outside diameter to provide a gradually increasing flexibility toward the distal end of the bump tubing section. As shown in FIG. 1, the intermediate portion may include a conventional braided or coiled material around the bump tubing section for increasing stiffness and pushability.

A tip section 15 is disposed distally of the bump tubing section and is made from a material having a flexural modulus substantially equal to or greater than the flexural modulus of the material in the taper section 14. In one embodiment, both can be made from the same material. A plurality of radiopaque markers 16 are provided within distal tip 15.

An embodiment of the invention is shown in cross-section in FIG. 2. A catheter 20 has a hub section 21, an intermediate section 22, a taper section 23, and a tip section 24. In this embodiment, catheter 20 includes a bump tubing piece 25 and a distal tubing piece 26 attached together at a joint 27. Pieces 25 and 26 can be made from polyolefins, polyethylene, polypropylene, polypropylene copolymers, or thermoplastic elastomers (such as TPO, TPU, TPV, polyester elastomers such as Hytrel, polyamide elastomers such as PEBAX, nylons, fluoropolymers including FEP, PFA, of ETFE, and the like). Within intermediate section 22, bump tubing piece 25 preferably has a substantially constant inside and outside diameter. The diameters may increase in hub section 21 to accommodate instruments or connecting devices. In taper section 23, bump tubing piece 25 has decreasing inside and outside diameters while approaching the distal end. Preferably, the inside diameter decreases less than the outside diameter so that bump tubing piece 25 also becomes thinner, thereby providing a greater increase in flexibility. After taper section 23, bump tubing piece 25 may have an optional straight segment 28 at its distal end. Distal tubing piece 26 preferably has matching inside and outside diameters with straight segment 28 providing a substantially seamless connection at 27.

As shown in greater detail in FIG. 3, distal tubing piece 26 preferably includes a distal liner 30 and a coaxial distal cover 31 with a plurality of annular markers 32 sandwiched between distal liner 30 and distal cover 31. By encapsulating markers 32, they are protected against damage and wear.

In one preferred embodiment, bump tubing piece 25 was extruded using a material known as PEBAX 7233 available from Arkema, Inc., of Philadelphia, Pa. This material has a flexural modulus of about 107,000 psi, which is a relatively inflexible material compared to conventional distal tips, and provides good pushability. In one embodiment of the catheter, the intermediate section of the bump tubing piece had an outside diameter of 0.063 inches and an inside diameter of 0.043 inches. Over a transition zone of about 9 inches in length, the outside diameter linearly decreased to about 0.054 inches and the inside diameter decreased to about 0.038 inches. The bump tubing section continued on for a straight segment having a length of about 7 inches. This embodiment accommodates a guide wire with a diameter of 0.035 inches. Continuing with this embodiment, distal liner 30 and distal cover 31 were likewise formed using PEBAX 7233 material-corrected. The final inside and outside diameters of the liner and cover after they are joined match those of the distal end of the bump tubing piece, but they start out as larger diameters which are shrunk during manufacturing as described below.

Since distal tip 26 is formed of materials having the same flexural modulus and since the diameter and thickness are the same, the flexibility of tip 26 is the same as at the distal end of bump tubing piece 25. Alternatively, an even harder material with a higher flexural modulus could be employed in distal tip 26.

The distal tubing piece forming tip 26 can be manufactured according to a method shown in FIGS. 4 and 5. A cylindrically shaped mandrel 35 having a diameter corresponding to the desired diameter of the internal lumen of the catheter receives distal liner tube 30. Liner tube 30 may originally have an inside diameter slightly larger than the diameter of mandrel 35 making it easy to fit liner tube 30 onto mandrel 35. Moreover, mandrel 35 may be coated with a lubricant to facilitate removal after shrinking of liner tube 30 as described below. After fitting distal liner tube 30 to mandrel 35, annular rings for markers 32 are placed over liner tube 30. The rings could be made of various radiopaque substances such as barium, bismuth, gold, hafnium, iridium, molybdenum, niobium, platinum, palladium, rhodium, rhenium, silver, tantalum, titanium, tungsten, or alloys or composites of these radiopaque substances. Placement of the rings on distal liner 30 can be evenly spaced or in any suitable pattern. After alignment, markers 32 are reduced in diameter by swaging (e.g., radial compression by a swaging tool placed over the rings).

FIG. 4 shows markers 32 prior to swaging. After swaging, markers 32 press into the surface of distal liner 30 as shown in FIG. 5. A distal cover 31 in the form of another polymeric tube with an inner diameter slightly larger than the outer diameter of the distal liner 30 is placed over distal liner 30 and markers 32. A piece of shrink tubing 36 is then placed over distal cover tubing 31 in preparation for joining the elements of the distal tubing piece. In its unshrunken state, shrink tubing 36 has an inside diameter slightly greater than the outside diameter of distal cover tubing 31. Upon heating to a sufficient temperature, shrink tubing 36 "recovers" its reduced diameter. Shrink tubing 36 may be comprised of a polyolefin heat shrink tubing available from Tyco Electronics Corporation of Berwin, Pa., for example. By heating all the components to a sufficiently high temperature (e.g., 120° C.), liner tubing 30 and cover tubing 31 soften sufficiently so that upon being squeezed equally from all sides by shrink tubing 36 they are squeezed against mandrel 35, causing the interface surface between liner tubing 30 and cover tubing 31 to fuse together. After cooling, heat shrink tubing 36 is removed by cutting into it with a razor blade and peeling it off.

Figure 6:
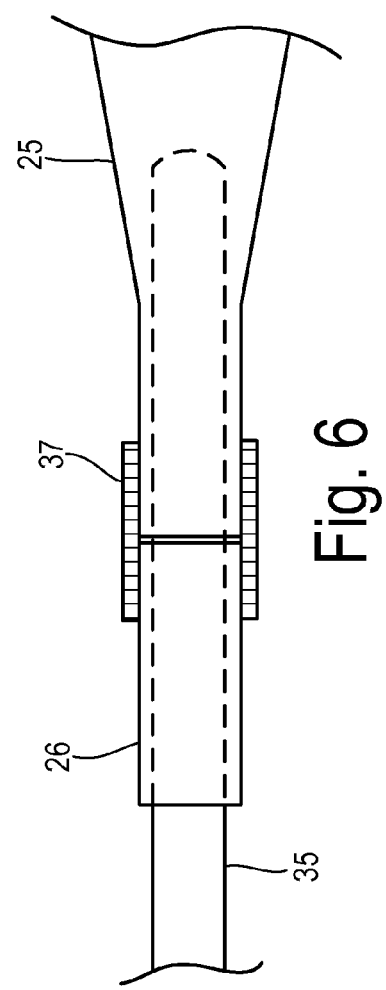
FIG. 6 illustrates the fusing of a distal tip section with a bump tubing section on a mandrel.

Distal tip section 26 can then be joined with a preformed bump tubing section 25 as shown in FIG. 6. Bump tubing section 25 is fit onto mandrel 35 to abut both the distal liner tube and the distal cover tube of distal end piece 26. The tube can be connected by welding methods known in the art such as ultrasonic, RF, laser, induction, vibration, or microwave welding. A bonding material could also be placed between the abutting surfaces. Preferably, the pieces are joined by fusing, welding, or bonding in the presence of heating while being covered with another heat shrink tubing 37. Thus, after abutting bump tubing piece 25 and distal tip piece 26, shrink tubing segment 37 is placed over the abutment and heat shrink tubing segment 37 and pieces 25 and 26 are heated for bonding them together. Heat shrink tubing 37 ensures a smooth transition across the interface. After cooling, heat shrink tubing 37 is cut using a razor blade and removed.

FIG. 7 shows an alternative embodiment employing a bump tubing piece 40 with an intermediate portion 41 and a taper portion 42. In this embodiment, the distal liner is comprised of an extension 43 formed as a continuous extrusion extending from tapered portion 42 of bump tubing piece 40. After being placed on a mandrel, radiopaque markers 45 are swaged onto extension 43. Then a distal cover 44 is fit over markers 45 and subsequently compressed over them using heat shrink tubing 46 shown in phantom. The distal end of the resulting distal tip formed by liner 43 and cover 44 may be trimmed and or shaped as desired (not shown).

FIG. 8 shows an alternative embodiment wherein only the longitudinal ends of distal cover 44 are fused using heat shrink tubing 47 and 48 applied at the opposite edges.

As previously discussed, portions of the bump tubing section may be covered with a braid formed from fibers wrapped over the bump tubing. Suitable materials for the fiber include Kevlar, NOMEX, Technora, Twaron, Vectran, glass, or stainless steel. The braiding can be woven in various patterns such as a conventional crisscross pattern shown in FIG. 9. The braiding may cover any desired portions of the intermediate section or the tapered section of the bump tubing. Furthermore, braiding could also be placed over a portion of the distal tip (not shown).

In an alternative embodiment shown in FIG. 10, a coiled layer 51 may be disposed over the intermediate portion or the taper portion of the bump tubing. The coil layer may be comprised of a metal wire made from stainless steel, gold, silver, platinum, copper, iridium, titanium, molybdenum, or combinations thereof. The braid or coiled layers increase the rigidity of the corresponding portions of the catheter and increase its pushability.

The braided or coiled fibers or wire 50 or 51 in FIGS. 9 and 10 would be preferably coated with a cover layer 52 or 53, respectively. The cover layer can be applied with a heat shrink operation, as an extrusion, or by dipping in a solution, for example. The coating layer may be between 0.0005 and 0.010 inches thick.

Figure 11:
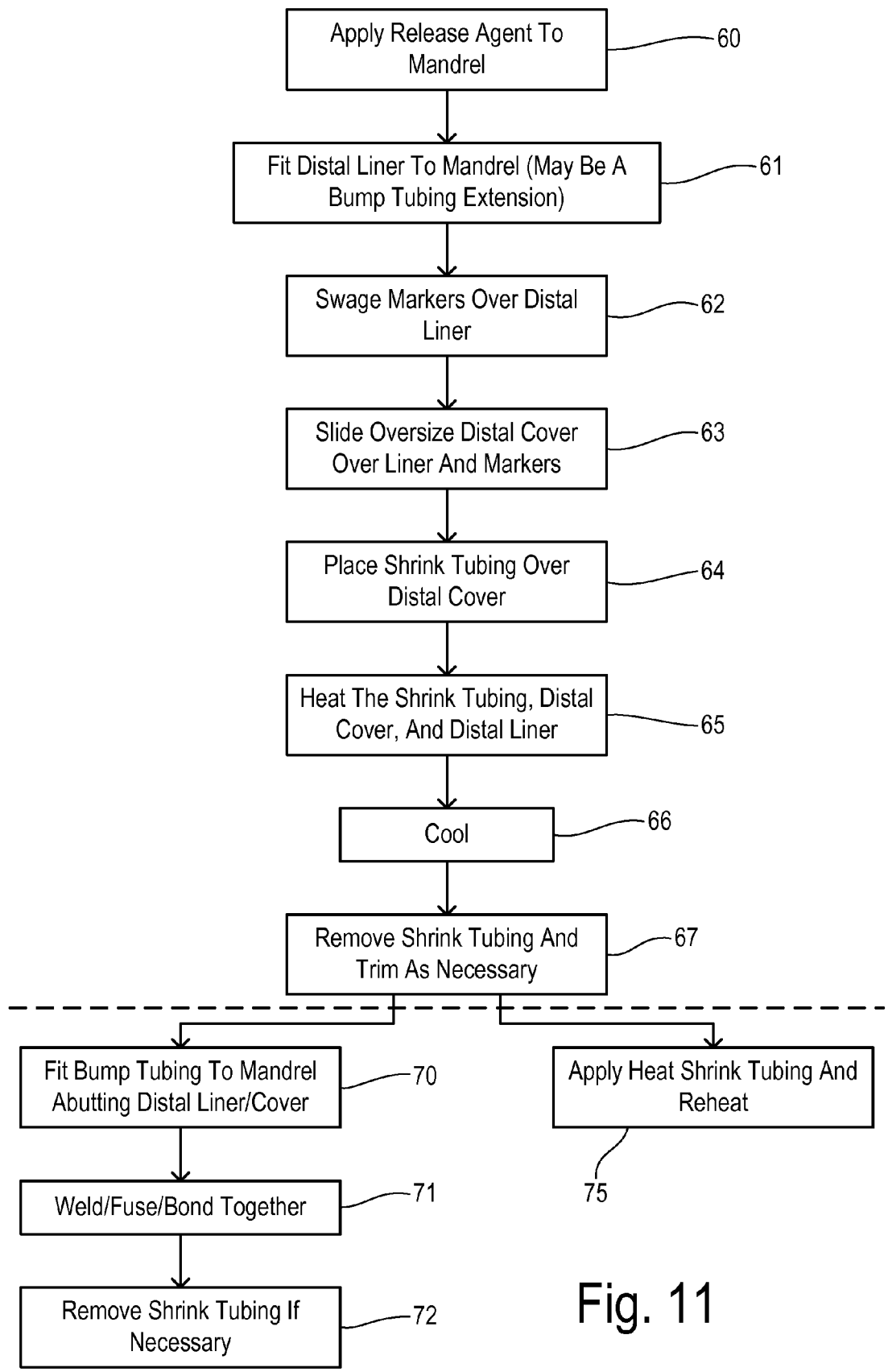
FIG. 11 is a flowchart representing various embodiments of a manufacturing method of the present invention.

The flowchart of FIG. 11 summarizes methods for manufacturing the catheters of the present invention. In step 60, a release agent or lubricant is applied to the mandrel. This may include a permanent or semi-permanent coating of PTFE or other fluoropolymer. In step 61, the distal liner is fit to the mandrel. As noted above, the distal liner may be a separate cylindrical tubing piece or may be an extension of the bump tubing section. In the case of a separate distal liner piece, multiple distal tips could be manufactured on the mandrel simultaneously either as distinct units or as one longer piece of tubing that is subsequently trimmed or cut into separate tip pieces after the addition of markers and a distal cover.

Radiopaque markers are swaged over the distal liner in step 62. In step 63, an oversized distal cover is slid over the liner and markers. In step 64, a piece of heat shrink tubing is placed over the distal cover. The heat shrink tubing, distal cover, and distal liner are heated in step 65 to cause the shrinkage of the heat shrink tubing and the fusing together of the distal cover and distal liner, thereby encapsulating the markers. The heat may be supplied by a hot air box placed around the tubing pieces and mandrel supplying hot air from a nozzle, whereby all the components are heated substantially evenly.

The hot air box is removed and the tubing pieces are allowed to cool in step 66. In step 67, the heat shrink tubing is cut longitudinally using a razor blade or other knife and then removed. The end or ends of the distal tip are trimmed as necessary.

In the event that the distal tip was not made using an extension of the bump tubing as the distal liner, then the distal tip must be joined with the bump tubing. In step 70, the bump tubing is fit to the mandrel to abut the distal liner/distal cover combination. In step 71, the bump tubing and the tip are welded/fused/bonded together. Step 71 may be performed in the presence of heat shrink tubing. In that case, the heat shrink tubing is removed in step 72.

In the event that the distal liner is being formed using an extension of the bump tubing, then following the removal of shrink tubing in step 67, there may be a second application of heat shrink tubing in step 75 in order to smooth the edges of the distal cover. After any necessary trimming, the completed catheter is removed from the mandrel.

What is claimed is:

1. A method of manufacturing a medical catheter having an intermediate zone, a bump tubing transition zone, and a distal zone, the method comprising the steps of:
   fitting a distal liner tube to a mandrel;
   swaging a plurality of radiopaque markers over the distal liner tube in the distal zone;
   fitting a distal cover tube over the distal liner tube and radiopaque markers in the distal zone;
   placing a shrink tubing segment over the distal cover tube;
   heating the shrink tubing segment to compress the distal cover tube onto the distal liner tube;
   removing the shrink tubing segment
   fitting a bump tubing onto the mandrel to abut both the distal liner tube and the distal cover tube; and
   further comprising the step of bonding the bump tubing to the distal liner tube and the distal cover tube at an abutment; placing a second shrink tubing segment over the abutment of the bump tubing with the distal liner tube and the distal cover tube; heating the second shrink tubing segment during the bonding of the bump tubing with the distal cover tube and the distal liner tube; and removing the second shrink tubing segment.

2. The method of claim 1 wherein the distal liner tube and distal cover tube are comprised of tubes of substantially equal length and unequal diameters.

3. The method of claim 1 further comprising the step of applying a braid over at least a portion of the intermediate zone.

4. The method of claim 1 further comprising the step of applying a coil over at least a portion of the intermediate zone.

* * * * *